US00PP17786P3

(12) United States Plant Patent

Anderson et al.

(10) Patent No.: US PP17,786 P3

(45) Date of Patent: Jun. 5, 2007

(54) *CHRYSANTHEMUM* PLANT NAMED '95-157-6'

(50) Latin Name: *Dendranthemum×hybrida*
Varietal Denomination: 95-157-6

(75) Inventors: Neil Owen Anderson, St. Paul, MN (US); Peter David Ascher, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 393 days.

(21) Appl. No.: 09/503,380

(22) Filed: Feb. 14, 2000

(65) Prior Publication Data

US 2002/0170103 P1 Nov. 14, 2002

(51) Int. Cl.
*A01H 5/00* (2006.01)

(52) U.S. Cl. ..... Plt./284

(58) Field of Classification Search ..... Plt./284
See application file for complete search history.

(56) References Cited

U.S. PATENT DOCUMENTS

| | | | |
|---|---|---|---|
| PP7,513 | P | 4/1991 | VandenBerg |
| PP7,754 | P | 12/1991 | VandenBerg |
| PP8,759 | P | 5/1994 | VandenBerg |
| PP8,987 | P | 11/1994 | VandenBerg |
| PP9,445 | P | 1/1996 | VandenBerg |
| PP9,578 | P | 6/1996 | Fuess |
| PP10,848 | P | 4/1999 | VandenBerg |
| PP10,909 | P | 5/1999 | Wain |
| PP10,943 | P | 6/1999 | Fuess |
| PP11,009 | P | 7/1999 | Davino, Jr. |
| PP11,032 | P | 8/1999 | Glicenstein |

OTHER PUBLICATIONS

Peter Ascher, et al., Maxi–Mums A Horticultural Breakthrough!, Minnesota Report 242–1997 University of Minnesota, Distribution Center Publication MR–67280B Minnesota Agricultural Experiment Station University of Minnesota (1997).

R.B. Clark, History of Culture of Hardy Chrysanthemums, National Chrysanthemum Society 18(3):144, 1962.

W.W. Garner, et al., Flowering and Fruiting of Plants as Controlled By The Length Of Day, 1920, p. 377–400, Yearbook of the Department of Agriculture, 1920, USA.

Peter Ascher, et al., Breeding and New Cultivars, Academic Perspective, Tips on Growing and Marketing Garden Mums, Ohio Florist's Association 1996.

Bradford Bearce, et al., Chrysanthemums A Manual of the Culture, Diseases, Insects and Ecocomics of Chrysanthemums, Jun. 1964, pp. 6–19, Prepared for The New York State Extension Service Chrysanthemum School with the Cooperation of the New York State Flower Growers Association, Inc.

Neil O. Anderson, et al., Rapid Generation Cycling of Chrysanthemum Using Laboratory Seed Development and Embryo Rescue Techniques, Journal of the American Society of Horticultural Science, Mar. 1990, pp. 329–336, vol. 115(2), Alexandria, Virginia 22314.

Leon Glicenstein, Breeding and New Cultivars, Commercial Perspective, Tips on Growing and Marketing Garden Mums, Ohio Florist's Association 1996.

M.A. Nazeer, et al., Cytogenetical Evolution of Garden Chrysanthemum, Current Science, Jun. 20, 1982, Vo. 51, No. 12.

Edward Higgins, Containers and Marketing, Tips on Growing and Marketing Garden Mums, Ohio Florist's Association 1996.

Naomasa Shimotomai, Bastardierungsversuche bei *Chrysanthemum* I., Journal of Science of the Hiroshima University, Series, B, Div. 2, vol. 1, Art. 3, 1931.

Naomasa Shimotomai, Bastardierungsversuche bei *Chrysanthemum* II. Eentstehung eines fruchtbaren Bastardes (haploid $4n^2$) aus der Kreuzung von *Ch. marginatum* (hapl. 5n) mit *Ch. morifolium* (hapl. 3n), Journal of Science of the Hiroshima University, Series B, Div. 2, vol. 1, Art. 8, 1932.

Ernest L. Scott, The Breeder's Handbook, 1957, pp. 1–76Handbook No. 4, National Chrysanthemum Society, Inc., U.S.A.

John Woolman, Chrysanthemums For Garden And Exhibition, 1953, pp. 1–103, W.H. & Collingridge Ltd., Tavistock Street, London WC2 and Transatlantic Arts Incorporated, Forest Hills, New York.

H.G. Witham Fogg, Chrysanthemum Growing, 1962, pp. 1–171, John Gifford Limited, London, W.C.2.

National Agricultural Statistics Service, USDA Additional Floriculture Information, pp. 1–84, National Agricultural Statistics Service, Floriculture Crops, 1998 Summary, Jun. 1999.

Handbook on Chrysanthemum Classification, A publication of the Classification Committee National Chrysanthemum Society, Inc. U.S.A., 1996 Edition.

C. Ackerson, Chapter 12 Development of the Chrysanthemum in China, pp. 146–155, National Chrysanthemum Society Bulletin 1967.

C. Ackerson, Chapter 11 Original Species of the Chrysanthemum, pp. 105–107, National Chrysanthemum Society Bulletin 1967.

G.J. Dowrick, The Chromosomes of Chrysanthemums, I: The Species, pp. 365–375, Heredity 6:365–375, 1952.

*Primary Examiner*—Kent Bell

(74) *Attorney, Agent, or Firm*—Penny J. Aguirre

(57) ABSTRACT

A new and distinct *Chrysanthemum* plant named '95-157-6' is provided.

4 Drawing Sheets

Genus/species: *Dendranthemum×hybrida.*
Cultivar designation: '95-157-6'.

BACKGROUND OF THE INVENTION

The present invention comprises a new and distinctive *chrysanthemum* plant, hereinafter referred to by the cultivar name '95-157-6'. This new cultivar was the result of a cross in 1989 between *Dendranthema weyrichii* and *Dendranthema grandiflora.* More specifically, the breeding program, which resulted in the production of the new cultivar was carried out in St. Paul, Minn. The breeding program commenced with a female plant of a *Dendranthema weyrichii,* which is unpatented, having the following characteristics: (a) the plant habit is prostrate and the plant spreads viarhizomes to form a large mat after the first year; (b) the plant dimensions are that the plant has a diameter of about 1.5' and is about 5–6" tall; (c) the plant is hardy in zones 4–9 (Southeast)/Zone 10 (west); (d) the flower of the plant is a single daisy, having light lavender colored ray florets and central disc florets with yellow pollen; (e) the plant has leaves that are dark green in color, with a very shiny leaf surface (glossy), and glabrous leaf margins that are deeply incised; and (f) the plants tends to rosette, needs cold treatment to flower consistently, flowering can be sporadic with gaps in the plant architecture and the plant is an obligate short-day plant. The male plant used to initiate the breeding program was a *Dendranthema grandiflora,* which is unpatented, having the following characteristics: (a) the plant habit is cushion; (b) the plant dimensions are that the plant is similar to other cushion types commercially available, such as, but not limited to the variety, 'Shasta' (U.S. Plant Pat. No. 9,314); (c) the plant is hardy in zones 6–9 (Southeast)/Zone 10 (west); (d) the flower is a single or duplex daisy, possibly orange or bronze ray florets, central disc florets with yellow pollen; (e) the plant has leaves that are similar to other cushion series of *chrysanthemums*; and (f) the plant is a facultative short-day plant. The resulting seeds, identified as '90-287-194' were collected. In 1991, a plant of '90-287-194' which is unpatented, was crossed as the male parent with plants identified as '77-AM3-3', a proprietary inbred parental selection, which is unpatented, as the female parent and the resulting seeds, identified as cross number '92-279-2' were collected. In 1994, a plant of '92-279-2', which is unpatented, was crossed as the male parent with plants of the cultivar 'Baby Tears' (unpatented) as the female parent and the resulting seeds, identified as cross number '95-157', were collected. In 1995, seedlings of the cross '95-157' were germinated and the flowering progeny evaluated. '95-157-6' was the sixth plant from the cross and was selected in the fall of 1995.

Asexual reproduction of the new cultivar by terminal or stem cuttings in St. Paul, Minn., U.S.A. has demonstrated that the characteristics of the new cultivar as herein described are firmly fixed and are retained through successive generations of such asexual reproduction.

SUMMARY OF THE INVENTION

It was found that the cultivar of the present invention:

(a) exhibits extreme hybrid vigor;

(b) develops, in its second and subsequent years after planting, when grown in the fall under natural daylength and without the application of growth regulators, into a flower herbaceous shrub having a plant height of from about 1.8 to about 2.25 feet and a spread form about 2.4 to about 5.0 feet, (c) exhibits, in its second and subsequent years after planting and during the fall season (August–October), a massive floral display, (d) displays flowers which are slightly toned with grey, giving the ray florets a slightly altered coloration, (e) exhibits superior winter hardiness, including frost tolerance, and (f) exhibits self-pinching.

The '95-157-6' cultivar has not been observed under all possible environmental conditions to date. Accordingly, it is possible that the phenotype may vary somewhat with variations in the environment, such as temperature, light intensity, and day length.

When the new cultivar of the present invention is compared to 'Stephanie' (U.S. Plant Pat. No. 9,445), it is found to exhibit a more spreading and prolific habit accompanied with a massive floral display in its second and subsequent years after planting. Reference is made to Table 1 below, which compares certain characteristics of '95-157-6' to 'Stephanie'.

TABLE 1

| Characteristics | '95-157-6' | 'Stephanie' |
|---|---|---|
| Capitulum form and type | Pentaplex daisy | Flat daisy |
| Plant Height | About 18 to 19 inches (first year); about 1.8 to about 2.25 feet (second year) | 10 to 12 inches |
| Branching Pattern | Spreading and very prolific | Spreading and very prolific |
| Flowering Response | 6 weeks | 7 weeks |
| Inflorescence Diameter | 7.1 cm | 5.8 to 6.1 cm |
| Ray florets, color, mature | White | White |

BRIEF DESCRIPTION OF THE PHOTOGRAPHS

The accompanying photographs show as nearly true as it is reasonably possible to make the same color illustrations of this type, typical flower and foliage characteristics of the new cultivar. The plants were grown in a greenhouse at St. Paul, Minn., USA.

DETAILED BOTANICAL DESCRIPTION

Figure 1:
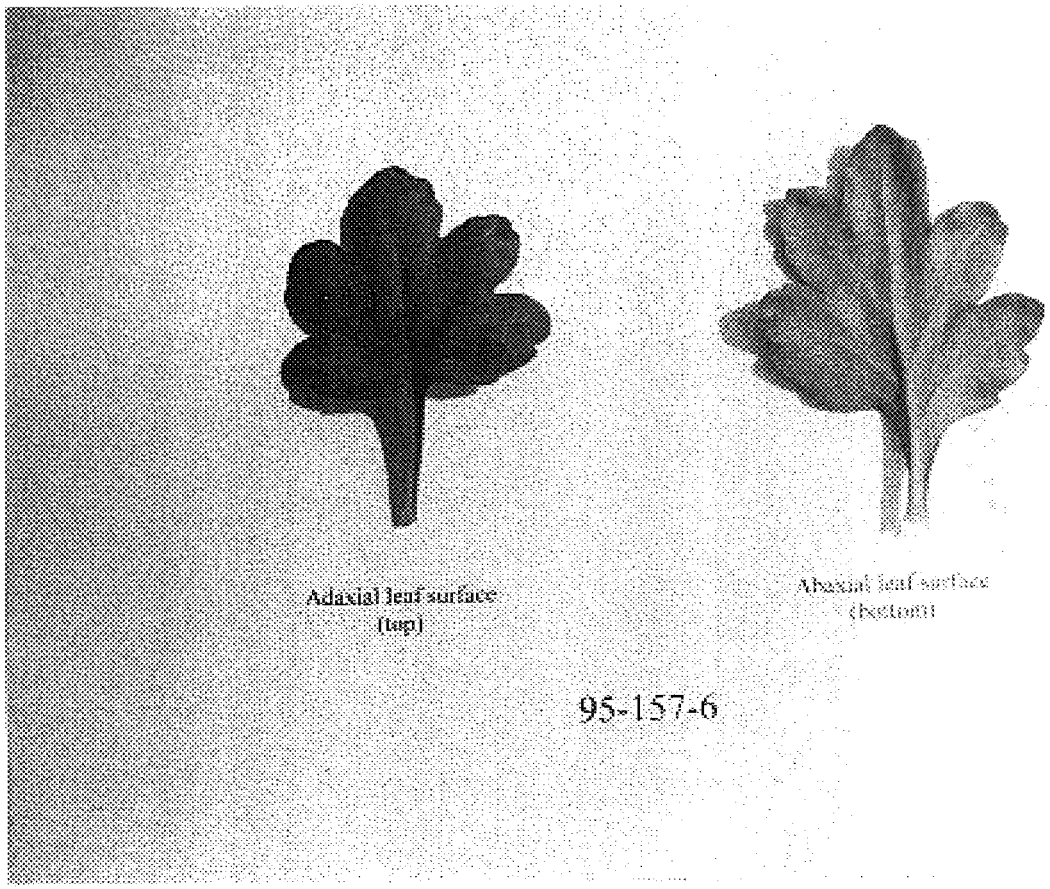
FIG. 1 shows an adaxial and abaxial view of the leaf shape of *chrysanthemum* variety '95-157-6'.
Figure 2:
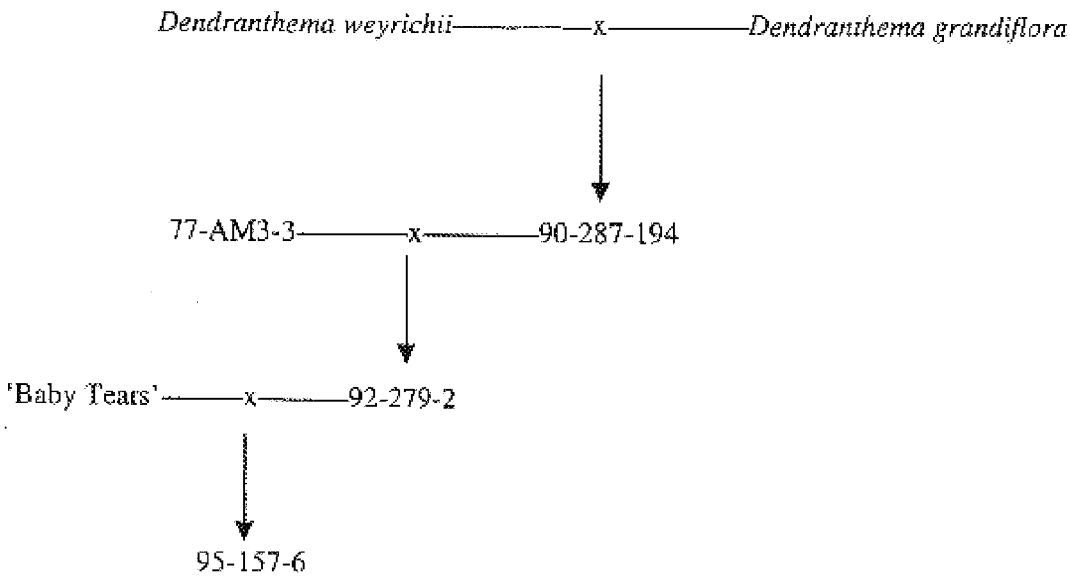
FIG. 2 shows the breeding history of *chrysanthemum* variety '95-157-6'.
Figure 3:
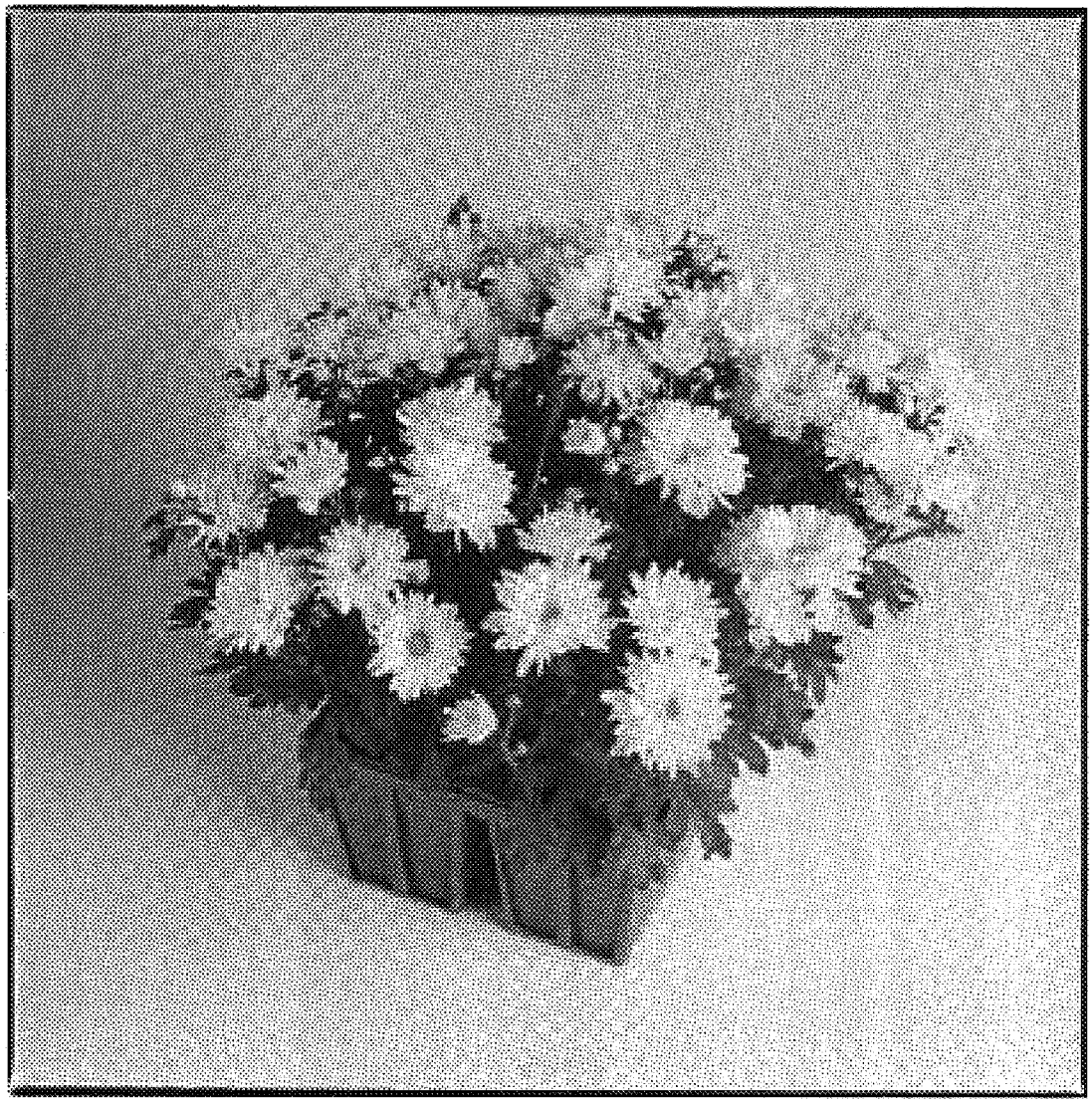
FIG. 3 is a color photograph of *chrysanthemum* variety '95-157-6' after two years of growth.
Figure 4:
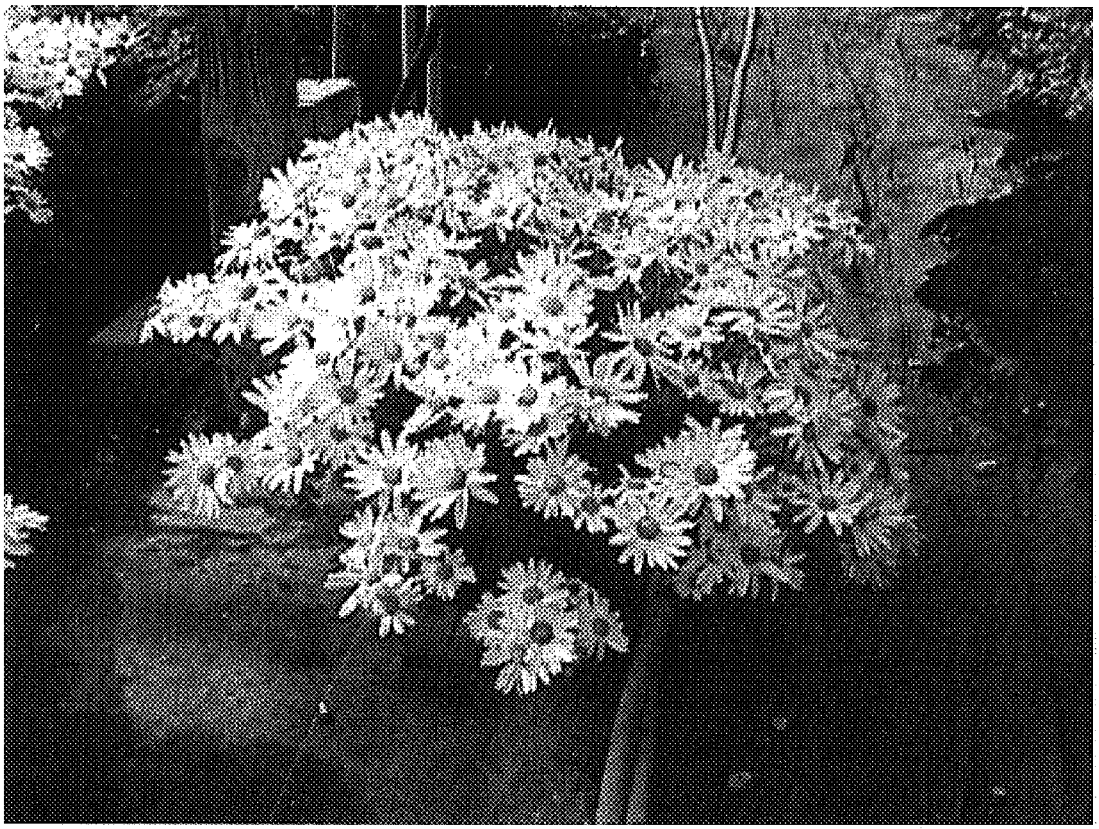

The chart used in the identification of colors described is the 1966 R.H.S. Colour Chart of The Royal Horticultural Society, London, England. The color values were determined on Oct. 15, 1999 in St. Paul, Minn. The readings were taken between 1:30 and 2:00 PM under approximately 2500 footcandles of light. The plants were produced from cuttings from stock plants and were grown under greenhouse conditions in St. Paul, Minn. comparable to those used in commercial practice while utilizing a soilless growth medium and maintaining temperatures of approximately 72° F. during the day and approximately 65° F. during the night. The plants described were one and two years of age from rooted cuttings.

Propagation:

*Type.*—Herbaceous stem cutting.

*Time of rooting.*—About 1 week.

*Rooting habit.*—Vigorous.

Botanical classification: *Dendranthemum×hybrida.*

Commercial classification: *Chrysanthemum* hybrid.

Plant description:

*Appearance, shape.*—Spherical mound.

*Appearance, growth habit.*—Cushion.

*Appearance, growth rate/vigor.*—Vigorous.

*Plant height.*—About 18 to about 19 inches (first year). About 1.8 to about 2.25 feet (second year).

*Lateral branch length.*—1 to 2.5 feet.

*Quantity of lateral branches after removal of apical meristem.*—One per node.
*Stem color.*—RHS Paris Green 58/1.

Foliage description:
*Number of leaves per plant.*—Greater than 8,000 (second year).
*Number of leaves per lateral branch.*—5 to 20.
*Leaf arrangement.*—Alternate.
*Leaf size, fully expanded, length.*—7.8 cm.
*Leaf size, fully expanded, width.*—4.8 cm.
*Leaf shape.*—Ovate and narrowing towards base.
*Leaf apex.*—Mucronulate.
*Leaf base.*—Cuneate.
*Leaf margin.*—Incised (Mulberry-like incisions).
*Leaf texture.*—Mildly hirsute.
*Petiole length.*—2.2 cm.
*Color, young foliage adaxial surface.*—RHS Scheeles Green 860/2.
*Color, young foliage abaxial surface.*—RHS Spinach Green o960/2.
*Color, fully expanded foliage abaxial surface.*—RHS Spinach Green o960.
*Color, fully expanded foliage abaxial surface.*—RHS Spinach Green o960/1 to RHS Spinach Green o960/3.
*Color, venation adaxial surface.*—RHS Spinach Green o960/2.
*Color, venation abaxial surface.*—RHS Spinach Green o960/3.
*Color, petiole.*—RHS Scheeles Green 860/1.
*Inflorescence description.*—Head (composite), pentaplex daisy.
*Flowering response.*—About 6 weeks (under short days).
*Quantity of inflorescences.*—About 1,000 (first year). About 3,000 (second year).
*Inflorescence size, diameter.*—7.1 cm.
*Inflorescence size, depth (height).*—3.4 cm.
*Inflorescence size, diameter of disc.*—1.0 cm.
*Opening inflorescences, bud shape.*—Dome shaped to upright tubular.
*Opening inflorescences, bud size, length.*—0.6 cm.
*Opening inflorescences, bud size, width.*—0.7 cm.
*Opening inflorescences, bud color.*—RHS Creamy White.
*Ray florets, shape.*—Linear lanceolate.
*Ray florets, size, length.*—2.7 cm.
*Ray florets, size, width.*—0.6 cm.
*Ray florets, apex.*—Retuse.
*Ray florets, base.*—Attenuate.
*Ray florets, margin.*—Entire.
*Ray florets, texture.*—Glabrous.
*Ray florets, aspect.*—From about 45° vertical to slightly pendant 45°.
*Number of ray florets per inflorescence.*—About 119.
*Ray florets, color, when opening, adaxial surface.*—RHS Sap Green 62/3.
*Ray florets, color, when opening, abaxial surface.*—RHS Uranium Green 63/3.
*Ray florets, mature, adaxial surface.*—RHS White.
*Ray florets, mature, abaxial surface.*—RHS White.
*Ray florets, fading to.*—RHS White.
*Disc florets, size, length.*—0.7 cm.
*Disc florets, size, width.*—0.2 cm.
*Number of disc florets per inflorescence.*—About 100.
*Disc florets, color, immature.*—RHS Straw Yellow 604.
*Disc florets, color, mature.*—RHS Chinese Yellow 606.
*Peduncle, aspect, strength.*—Stiff.
*Peduncle, aspect, angle to stem.*—45°.
*Peduncle, length, first peduncle.*—3 cm.
*Peduncle, length, fourth peduncle.*—4.6 cm.
*Peduncle, texture.*—Midly hirsute.
*Peduncle, color.*—RHS Viridian Green 55/3.
*Reproductive organs, androecium, floret location.*—Disc florets.
*Anther color.*—RHS Canary Yellow 2/1.
*Pollen abundance.*—Abundant.
*Pollen, color.*—RHS Buttercup Yellow 5.
*Reproductive organs, gynoecium, floret location.*—Disc/ray florets.
*Style color.*—RHS Buttercup Yellow 5/2.

Stamen description: Stamens are located within each individual disk floret. Each stamen is borne on a filament that, when mature (dehiscent with pollen shedding longitudinally along the long axis of the anther), places the stamens above the stigma (i.e., the top portion of the pistil).

Pistil number: Each ray floret possesses one pistil (there are approximately 60 per inflorescence). Likewise, each disk floret also possesses a pistil (there are approximately 191 per inflorescence). Therefore, the total number of pistils/inflorescence is 251 (60+191). The size of the pistil (length) is approximately 1 cm.

Disease resistance: None Known as '95-157-6' has not been tested for any diseases.

Seed production and fruit: About 152 ovules/flower. The fruit is an achene, a dry, indehiscent fruit with a single locule and a single seed, and with the seed attached to the ovary wall at a single point. The achene does not have any pappus of awns for bristles; its general shape is a half-inflated football oval with pointed ends. Seed size is about 0.2–0.5 cm in length and about 0.1–0.2 cm in width. The surface texture is ridged. The color designation for the seed is RHS Brown Group 200D.

Fragrance: Fragrance is noticeable when handling or bruising the foliage.

Longevity of the bloom: Flower longevity is temperature dependent. Under normal conditions in the field, during the fall season, inflorescences will typically last about 2–4 plus weeks.

Winter hardiness: Hardy in zones 3–10 in uncovered field conditions without the need for added protection such as snow fences, mulch, etc.

Frost tolerance: Yes, extends blooming season to the first freeze in the north (In zones 3–4 the first frost usually takes place between September 1–15. In zones 3–4, the first freeze usually takes place between October 1–20.

We claim:

1. A new and distinct *Chrysanthemum* plant named '95-157-6' substantially as herein shown and described.

* * * * *

UNITED STATES PATENT AND TRADEMARK OFFICE

CERTIFICATE OF CORRECTION

PATENT NO. : PP 17,786 P3
APPLICATION NO. : 09/503380
DATED : June 5, 2007
INVENTOR(S) : Neil Owen Anderson and Peter David Ascher It is certified that error appears in the above-identified patent and that said Letters Patent is hereby corrected as shown below:

Col 1 Above Background of the Invention

Please insert the following in the appropriate location on the specification

STATEMENT REGARDING FEDERALLY SPONSORED RESEARCH

This invention was made with government support under MIN-21-50 and MIN-21-52 awarded by the U.S. Dept. of Agriculture. The government has certain rights in the invention.

Signed and Sealed this

First Day of July, 2008

JON W. DUDAS
*Director of the United States Patent and Trademark Office*